(12) United States Patent
Gangumalla et al.

(10) Patent No.: US 12,252,395 B2
(45) Date of Patent: *Mar. 18, 2025

(54) METHOD AND SYSTEM FOR SENSOR CONFIGURATION

(71) Applicant: INVENSENSE, INC., San Jose, CA (US)

(72) Inventors: Vamshi Gangumalla, San Jose, CA (US); Uday Mudoi, San Mateo, CA (US); Karthik Katingari, San Jose, CA (US); Mahdi Heydari, Stanford, CA (US)

( * ) Notice: Subject to any disclaimer, the term of this patent is extended or adjusted under 35 U.S.C. 154(b) by 252 days.

This patent is subject to a terminal disclaimer.

(21) Appl. No.: 17/970,143

(22) Filed: Oct. 20, 2022

(65) Prior Publication Data
US 2023/0110372 A1 Apr. 13, 2023

Related U.S. Application Data

(63) Continuation-in-part of application No. 16/946,511, filed on Jun. 24, 2020, now Pat. No. 11,479,459.

(60) Provisional application No. 62/887,538, filed on Aug. 15, 2019.

(51) Int. Cl.
| | |
|---|---|
| *B81B 7/04* | (2006.01) |
| *B81B 3/00* | (2006.01) |
| *G01C 19/00* | (2013.01) |
| *G01D 3/10* | (2006.01) |
| *G01P 15/18* | (2013.01) |
| *G01D 3/08* | (2006.01) |
| *G01N 33/00* | (2006.01) |
| *G01P 21/00* | (2006.01) |

(52) U.S. Cl.
CPC .............. *B81B 7/04* (2013.01); *B81B 3/0021* (2013.01); *G01C 19/00* (2013.01); *G01D 3/10* (2013.01); *G01P 15/18* (2013.01); *B81B 2201/0235* (2013.01); *B81B 2201/0242* (2013.01); *G01D 3/08* (2013.01); *G01D 2218/10* (2021.05); *G01N 33/0031* (2013.01); *G01N 2223/501* (2013.01); *G01P 21/00* (2013.01)

(58) Field of Classification Search
CPC ............. G01P 21/00; G01P 2015/0845; G01P 2015/0848; G01P 2015/0851; G01D 3/10; G01D 3/08; G01D 2218/10; G01N 33/0031; G01N 2223/501; G01C 25/00; B81B 7/04
See application file for complete search history.

(56) References Cited

U.S. PATENT DOCUMENTS

| | | | | |
|---|---|---|---|---|
| 2015/0344295 | A1* | 12/2015 | Cattani | .................. H04R 3/007 318/116 |
| 2019/0353502 | A1* | 11/2019 | Doshi | .................... G01D 21/00 |

* cited by examiner

*Primary Examiner* — Benjamin R Schmitt

(57) ABSTRACT

Described herein are methods and systems for controlling a sensor assembly with a plurality of same type sensors. Sensors are operated in active and inactive states. The activation state of at least one of the sensors is changed based on an operational parameter that relates to an environmental condition differentially affecting the plurality of same type sensors.

13 Claims, 5 Drawing Sheets

METHOD AND SYSTEM FOR SENSOR CONFIGURATION

CROSS-REFERENCE TO RELATED APPLICATIONS

This application is a continuation-in-part of and claims priority to U.S. Provisional Patent Application No. 62/887,538, filed Aug. 15, 2019 and to U.S. patent application Ser. No. 16/946,511 (now allowed), the contents of each are incorporated by reference in their entirety.

FIELD OF THE PRESENT DISCLOSURE

This disclosure generally relates to sensors and more specifically to sensor assemblies with configurable performance and reliability operation.

BACKGROUND

The development of microelectromechanical systems (MEMS) has enabled the incorporation of a wide variety of sensors in a variety of applications. Notably, information from motion sensors such as gyroscopes that measure angular velocity and accelerometers that measure specific forces along one or more orthogonal axes may be used to determine the orientation, change in relative orientation and/or translational displacement of a device incorporating the sensors for use as a user input, to determine positional or navigational information for the device, or for other suitable purposes. The sensors can be employed with automated, robotic or piloted terrestrial, maritime or aerial vehicles, and other similar devices capable of motion. However, these technologies are also employed with a wide variety of other devices, including mobile/portable devices, such as cell phones, laptops, tablets, gaming devices and other portable, electronic devices. Such sensors may also be employed in stationary, fixed or mounted devices. Still further, other types of sensors capable of measuring or responding to environmental phenomena or other conditions affecting the devices may also be employed However, due to the nature of electronics and mechanics, sensors in general and MEMS sensors in particular may experience variations in operation or may experience anomalies that may temporarily or permanently affect operation. For example, conventional sensor systems do not provide sufficient information about faulty operation and lack mechanisms for recovering from such faults. Further, typical sensor assemblies may be configured to provide relatively improved reliability or performance but fail to offer the ability to dynamically adjust those characteristics. For example, a system that features redundant sensors may not offer any performance enhancement despite having extra hardware while a system that utilizes a plurality of sensors to improve performance may not be sufficiently adaptable to offer increased reliability.

Correspondingly, there is a need for a sensor systems that provide monitoring capability to assess the current state of the sensors. Likewise, it would be desirable to dynamically adjust the operation of a sensor assembly to compensate for changes in sensor operation. Still further, there is a need for sensor systems that allow recovery mechanisms when anomalies occur. Moreover, it would be desirable to be able to adjust performance or reliability characteristics of a sensor system to accommodate different needs. As will be described in the following materials, the techniques of this disclosure these and other benefits.

SUMMARY

As will be described in detail below, this disclosure includes a method for controlling a sensor assembly. Notably, the method involves providing a sensor assembly having a plurality of same type sensors. A first variable number of same type sensors are operated in an active state and a second variable number of same type sensors are operated in an inactive state. An activation state of at least one of the plurality of sensors is based at least in part on an operational parameter, wherein the operational parameter relates to an environmental condition differentially affecting the plurality of same type sensors.

The techniques of this disclosure also involve a sensor assembly having a plurality of same type sensors. The system may include a plurality of same type sensors and at least one processor configured to operate a first variable number of sensors in an active state, operate a second variable number of sensors in an inactive state and change an activation state of at least one of the plurality of sensors based at least in part on an operational parameter, wherein the operational parameter relates to an environmental condition differentially affecting the plurality of same type sensors.

This disclosure also is directed to a device that may have a sensor assembly comprising a plurality of same type sensors and at least one processor. The at least one processor may be configured to operate a first variable number of sensors in an active state, operate a second variable number of sensors in an inactive state and change an activation state of at least one of the plurality of sensors based at least in part on an operational parameter, wherein the operational parameter relates to an environmental condition differentially affecting the plurality of same type sensors.

DETAILED DESCRIPTION

Figure 1:
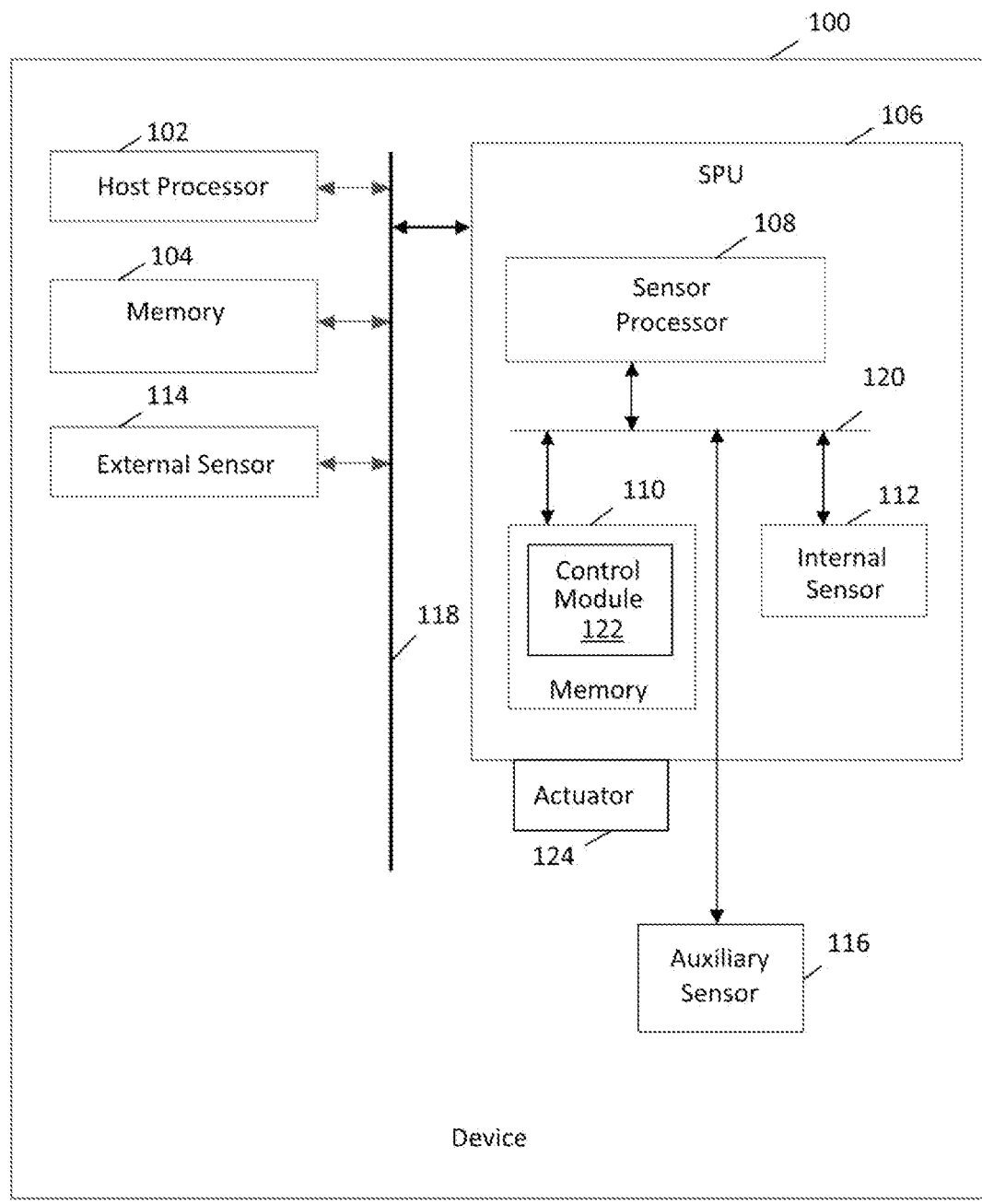
FIG. 1 is schematic diagram of device having a sensor assembly having a plurality of same type sensors according to an embodiment.

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings or chip embodiments. These and similar directional terms should not be construed to limit the scope of the disclosure in any manner.

In this specification and in the claims, it will be understood that when an element is referred to as being "connected to" or "coupled to" another element, it can be directly connected or coupled to the other element or intervening elements may be present. In contrast, when an element is referred to as being "directly connected to" or "directly coupled to" another element, there are no intervening elements present.

Some portions of the detailed descriptions which follow are presented in terms of procedures, logic blocks, processing and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those requiring physical manipulations of physical quantities. Usually, although not necessarily, these quantities take the form of electrical or magnetic signals capable of being stored, transferred, combined, compared, and otherwise manipulated in a computer system.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present application, discussions utilizing the terms such as "accessing," "receiving," "sending," "using," "selecting," "determining," "normalizing," "multiplying," "averaging," "monitoring," "comparing," "applying," "updating," "measuring," "deriving" or the like, refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments described herein may be discussed in the general context of processor-executable instructions residing on some form of non-transitory processor-readable medium, such as program modules, executed by one or more computers or other devices. Generally, program modules include routines, programs, objects, components, data structures, etc., that perform particular tasks or implement particular abstract data types. The functionality of the program modules may be combined or distributed as desired in various embodiments.

In the figures, a single block may be described as performing a function or functions; however, in actual practice, the function or functions performed by that block may be performed in a single component or across multiple components, and/or may be performed using hardware, using software, or using a combination of hardware and software. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure. Also, the exemplary wireless communications devices may include components other than those shown, including well-known components such as a processor, memory and the like.

The techniques described herein may be implemented in hardware, software, firmware, or any combination thereof, unless specifically described as being implemented in a specific manner. Any features described as modules or components may also be implemented together in an integrated logic device or separately as discrete but interoperable logic devices. If implemented in software, the techniques may be realized at least in part by a non-transitory processor-readable storage medium comprising instructions that, when executed, performs one or more of the methods described above. The non-transitory processor-readable data storage medium may form part of a computer program product, which may include packaging materials.

The non-transitory processor-readable storage medium may comprise random access memory (RAM) such as synchronous dynamic random access memory (SDRAM), read only memory (ROM), non-volatile random access memory (NVRAM), electrically erasable programmable read-only memory (EEPROM), FLASH memory, other known storage media, and the like. The techniques additionally, or alternatively, may be realized at least in part by a processor-readable communication medium that carries or communicates code in the form of instructions or data structures and that can be accessed, read, and/or executed by a computer or other processor. For example, a carrier wave may be employed to carry computer-readable electronic data such as those used in transmitting and receiving electronic mail or in accessing a network such as the Internet or a local area network (LAN). Of course, many modifications may be made to this configuration without departing from the scope or spirit of the claimed subject matter.

The various illustrative logical blocks, modules, circuits and instructions described in connection with the embodiments disclosed herein may be executed by one or more processors, such as one or more sensor processing units (SPUs), motion processing units (MPUs), digital signal processors (DSPs), general purpose microprocessors, application specific integrated circuits (ASICs), application specific instruction set processors (ASIPs), field programmable gate arrays (FPGAs), or other equivalent integrated or discrete logic circuitry. The term "processor," as used herein may refer to any of the foregoing structure or any other structure suitable for implementation of the techniques described herein. In addition, in some aspects, the functionality described herein may be provided within dedicated software modules or hardware modules configured as described herein. Also, the techniques could be fully implemented in one or more circuits or logic elements. A general purpose processor may be a microprocessor, but in the alternative, the processor may be any conventional processor, controller, microcontroller, or state machine. A processor may also be implemented as a combination of computing devices, e.g., a combination of an SPU and a microprocessor, a plurality of microprocessors, one or more microprocessors in conjunction with an SPU core, or any other such configuration.

Unless defined otherwise, all technical and scientific terms used herein have the same meaning as commonly understood by one having ordinary skill in the art to which the disclosure pertains.

Finally, as used in this specification and the appended claims, the singular forms "a, "an" and "the" include plural referents unless the content clearly dictates otherwise.

As noted above, the techniques of this disclosure relate to sensor assemblies that can be controlled by changing activation states of its sensors to achieve different performance and/or reliability parameters. In one aspect, the replacement of a defective or anomalous sensor with a redundant sensor can be termed sensor failover. An operational parameter may be employed when changing the activation states. For example, the operational parameter may relate to a desired performance compared to reliability. The operational parameter may also reflect information from the sensors about their status, including whether they have suffered anomalies, faults or other events. Sensor status information may also be determined by comparing sensor measurements. Operational parameters may also relate to other factors, including regulatory requirements, estimated working lifetimes, desired power consumption and others. In particular, the sensor assembly includes at least one plurality of the same type of sensors. As used herein, a sensor may refer to a component that provides measurements for one axis of a suitable frame of reference, such as the x, y or z-axis of a Cartesian coordinate system. Correspondingly, the plurality of sensors in this context refers to sensors of the same type (e.g., accelerometers, gyroscopes, or magnetometers, etc.) that sense forces along the same axis. However, a sensor can also refer to multi-axes devices that provide measurements along two or more, usually orthogonal, axes, with one illustrative example being a sensor that provides measurements along each of the x, y and z-axes. As a result, a plurality of same type sensors each measure the same phenomena along the same axis or combination of axes. It should also be appreciated that sensors of the same type need not be identical to each other. For example, a sensor may have different performance characteristics, such as greater or lesser accuracy, as compared to another same type sensor.

One notable application of such sensor assemblies is to provide environmental and/or motion awareness for a device that moves three dimensionally so that its motion and/or orientation in space therefore sensed. The techniques of this disclosure and the described systems for controlling sensor assemblies may be used in any context, including with vehicles and other sensor platforms. For example, robotic or autonomous vehicles as well as piloted vehicles may benefit from the sensor assemblies of this disclosure for navigation, safety, equipment control or other applications. Notably, high performance and high reliability are particularly desirable for industrial applications to deliver required accuracy, robustness and to avoid operational disruption. The sensor failover mechanisms and other techniques of this disclosure are applicable to a variety of navigation, stabilization and orientation measurement applications in industrial systems including precision agriculture equipment, construction machinery, geospatial survey equipment, manned and unmanned aerial vehicles and robots. An example application would be a construction vehicle that can combine IMU measurements with data from a global navigation system, such as GPS, to determine precise position, attitude and motion in real time. The performance and reliability delivered by the techniques of this disclosure are beneficial for increased automation, efficiency and safety of such mobile industrial machinery. Devices configured for motion typically have a motor, engine, gear box or other mechanical system that operates at one or more frequencies and may create vibration as an environmental condition that may differentially affect sensors of the device. Details regarding one embodiment of device 100 including features of this disclosure are depicted as high level schematic blocks in FIG. 1. However, the techniques of this disclosure can also be extended to other mobile/portable or stationary devices. Common examples of portable devices include a mobile phone (e.g., cellular phone, a phone running on a local network, or any other telephone handset), wired telephone (e.g., a phone attached by a wire), personal digital assistant (PDA), video game player, video game controller, navigation device, activity or fitness tracker device (e.g., bracelet or clip), smart watch, other wearable device, mobile internet device (MID), personal navigation device (PND), digital still camera, digital video camera, binoculars, telephoto lens, portable music, video, or media player, remote control, or other handheld device, or a combination of one or more of these devices. Similarly, stationary, fixed and/or mounted devices may include any device having a sensor, such as a generator or wind turbine. As will be discussed below, such devices may have some system, such as an engine, motor or other driven apparatus operating at one or more frequencies or may have a sensor that exhibits differential performance depending on another environmental condition.

As shown, device 100 includes a host processor 102, which may be one or more microprocessors, central processing units (CPUs), or other processors to run software programs, which may be stored in memory 104, associated with the functions of device 100. Multiple layers of software can be provided in memory 104, which may be any combination of computer readable medium such as electronic memory or other storage medium such as hard disk, optical disk, etc., for use with the host processor 102. For example, an operating system layer can be provided for device 100 to control and manage system resources in real time, enable functions of application software and other layers, and interface application programs with other software and functions of device 100. Similarly, different software application programs such as menu navigation software, games, camera function control, navigation software, communications software, such as telephony or wireless local area network (WLAN) software, or any of a wide variety of other software and functional interfaces can be provided. In some embodiments, multiple different applications can be provided on a single device 100, and in some of those embodiments, multiple applications can run simultaneously.

Device 100 includes at least one sensor assembly, as shown here in the form of integrated sensor processing unit (SPU) 106 featuring sensor processor 108, memory 110 and internal sensor arrangement 112, which may have at least a plurality of sensors of the same type according to the techniques of this disclosure, each of which may be single axis sensors or multi-axis sensors as discussed above. Depending on the embodiment, each of the plurality of same type sensors may be implemented within SPU 106 or each may be in separate SPUs for example. Memory 110 may store algorithms, routines or other instructions for processing data output by internal sensor arrangement 112 and/or other sensors as described below using logic or controllers of sensor processor 108, as well as storing raw data and/or motion data output by internal sensor configuration 112 or other sensors. Memory 110 may also be used for any of the functions associated with memory 104. Internal sensor arrangement 112 may be a plurality of one or more sensors of the same type for measuring motion, position, and/or orientation of device 100 in space, such as an accelerometer, a gyroscope, a magnetometer, a pressure sensor or others. For example, SPU 106 measures one or more axes of rotation and/or one or more axes of acceleration of the device. It should be appreciated that this exemplary embodiment is discussed with an emphasis on motion sensors, but the techniques of this disclosure can be applied to any type of sensor, including those that measure environmental phenomena or conditions other than movement of the sensor assembly.

In one embodiment, internal sensor arrangement 112 may include rotational motion sensors or linear motion sensors. For example, the rotational motion sensors may be gyroscopes to measure angular velocity along one or more orthogonal axes and the linear motion sensors may be accelerometers to measure linear acceleration along one or more orthogonal axes. Sensors of the same type measure equivalent aspects of motion or environmental phenomena, with the same sensitive axes or the same combination of sensitive axes. In one aspect, multiple three-axis gyroscopes and/or multiple three-axis accelerometers may be employed, such that a sensor fusion operation performed by sensor processor 108, or other processing resources of device 100, combines data from the active sensors of internal sensor arrangement 112 to provide a six axis determination of motion or six degrees of freedom (6DOF). Equally, the techniques may be applied in more granularly by providing a plurality of same type single-axis sensors for different numbers of axes as desired. As desired, internal sensor arrangement 112 may be implemented using Micro Electro Mechanical System (MEMS) to be integrated with SPU 106 in a single package. Exemplary details regarding suitable configurations of host processor 102 and SPU 106 may be found in, commonly owned U.S. Pat. No. 8,250,921, issued Aug. 28, 2012, and U.S. Pat. No. 8,952,832, issued Feb. 10, 2015, which are hereby incorporated by reference in their entirety. Suitable implementations for SPU 106 in device 100 are available from TDK InvenSense, Inc. of San Jose, Calif.

Alternatively, or in addition, device 100 may implement the plurality of same type sensors in the form of external sensor arrangement 114. Each of the plurality of sensors may be in one or more external sensor arrangements 114 or in a combination of internal sensor arrangement 112 and external sensor arrangement 114. Thus, external sensor arrangement 114 may represent one or more sensors as described above, such as an accelerometer and/or a gyroscope. As used herein, "external" means a sensor that is not integrated with SPU 106 and may be remote or local to device 100. Also alternatively or in addition, SPU 106 may receive data from an auxiliary sensor arrangement 116 configured to measure one or more aspects about the environment surrounding device 100, and which may also at least one of the plurality of same type sensors or may feature other sensors. For example, a pressure sensor and/or a magnetometer may be used to refine motion determinations made using internal sensor arrangement 112. In one embodiment, auxiliary sensor arrangement 116 may include a magnetometer measuring along three orthogonal axes and output data to be fused with the gyroscope and accelerometer inertial sensor data to provide a nine axis determination of motion. In another embodiment, auxiliary sensor arrangement 116 may also include a pressure sensor to provide an altitude determination that may be fused with the other sensor data to provide a ten axis determination of motion. Although described in the context of one or more sensors being MEMS based, the techniques of this disclosure may be applied to any sensor design or implementation. Depending on the embodiment, any combination sensors of internal sensor arrangement 112, external sensor arrangement 114 and/or auxiliary sensor arrangement 116 may provide the plurality of same type sensors, with any remainder employing conventional sensor arrangements. In sum, the sensors of the plurality of same type sensors may be implemented using one or different combinations of internal sensor arrangement 112, external sensor arrangement 114 and/or auxiliary sensor arrangement 116.

In the embodiment shown, host processor 102, memory 104, SPU 106 and other components of device 100 may be coupled through bus 118, while sensor processor 108, memory 110, internal sensor arrangement 112 and/or auxiliary sensor arrangement 116 may be coupled though bus 120, either of which may be any suitable bus or interface, such as a peripheral component interconnect express (PCIe) bus, a universal serial bus (USB), a universal asynchronous receiver/transmitter (UART) serial bus, a suitable advanced microcontroller bus architecture (AMBA) interface, an Inter-Integrated Circuit (I2C) bus, a serial digital input output (SDIO) bus, a serial peripheral interface (SPI) or other equivalent. Depending on the architecture, different bus configurations may be employed as desired. For example, additional buses may be used to couple the various components of device 100, such as by using a dedicated bus between host processor 102 and memory 104.

Code, algorithms, routines or other instructions for processing sensor data may be employed by control module 122, schematically represented in this figure as being stored in memory 110 for execution by sensor processor 108, to perform any of the operations associated with the techniques of this disclosure. As will be discussed in further detail below, control module 122 selectively changes the activation state of one or more of the plurality of same type sensors. It should be appreciated that this can involve either a binary active/inactive state or can involve additional hybrid states, such as standby or selection among various performance levels. A sensor may also be considered inactive even when fully powered under situations when its output is not being used as a normally active sensor, such as during a test period when its performance is being monitored to assess whether a recovery operation was successful or when undergoing calibration for example. Control module 122 can also manage the tracking of the performance, reliability and operational parameters and optionally may combine the measurements provided by the plurality of same type sensors as discussed in further detail below. Control module 122 may also report the current or past status of any sensors of the sensor assembly. Alternatively, or in addition, the functionality of control module 122 may be implemented using host processor 102 and memory 104 or any other suitable processing resources. In this case, SPU 106 may transfer the sensor data acquired to host processor 102 and/or memory 104.

Further, device 100 may have actuator 124 coupled or otherwise associated with SPU 106 that is configured to change a current condition of one or more sensors. For example, actuator 124 may be configured to deliver a thermal, mechanical, electric, electrostatic or other physical shock to internal sensor arrangement 112 to attempt recovery of a malfunctioning sensor as discussed below. Alternatively or in addition, one or more similar actuators can also be associated with external sensor arrangement 114 and/or auxiliary sensor arrangement 116 for the same purpose. In some embodiments, it may be desirable to employ actuator 124 each time the activation state of a sensor is changed.

Any combination of sensor components of device 100 may be formed on different chips or may be integrated and reside on the same chip. Likewise, the sensor components can be otherwise enclosed or covered to create a unitary package. A chip may be defined to include at least one substrate typically formed from a semiconductor material. A single chip or package may be formed from multiple substrates, where the substrates are mechanically bonded to preserve the functionality. A multiple chip includes at least two substrates, wherein the two substrates are electrically connected, but do not require mechanical bonding. A package provides electrical connection between the bond pads on the chip to a metal lead that can be soldered to a PCB. A package typically comprises a substrate and a cover. Integrated Circuit (IC) substrate may refer to a silicon substrate with electrical circuits, typically CMOS circuits. One or more sensors may be incorporated into the package if desired using any suitable technique. In some embodiments, a sensor may be MEMS-based, such that a MEMS cap provides mechanical support for the MEMS structure. The MEMS structural layer is attached to the MEMS cap. The MEMS cap is also referred to as handle substrate or handle wafer. In some embodiments, the first substrate may be vertically stacked, attached and electrically connected to the second substrate in a single semiconductor chip, while in other embodiments, the first substrate may be disposed laterally and electrically connected to the second substrate in a single semiconductor package. In one embodiment, the first substrate is attached to the second substrate through wafer bonding, as described in commonly owned U.S. Pat. No. 7,104,129, which is incorporated herein by reference in its entirety, to simultaneously provide electrical connections and hermetically seal the MEMS devices. This fabrication technique advantageously enables technology that allows for the design and manufacture of high performance, multi-axis, inertial sensors in a very small and economical package. Integration at the wafer-level minimizes parasitic capacitances, allowing for improved signal-to-noise relative to a discrete solution. Such integration at the wafer-level also enables the incorporation of a rich feature set which minimizes the need for external amplification.

Figure 2:
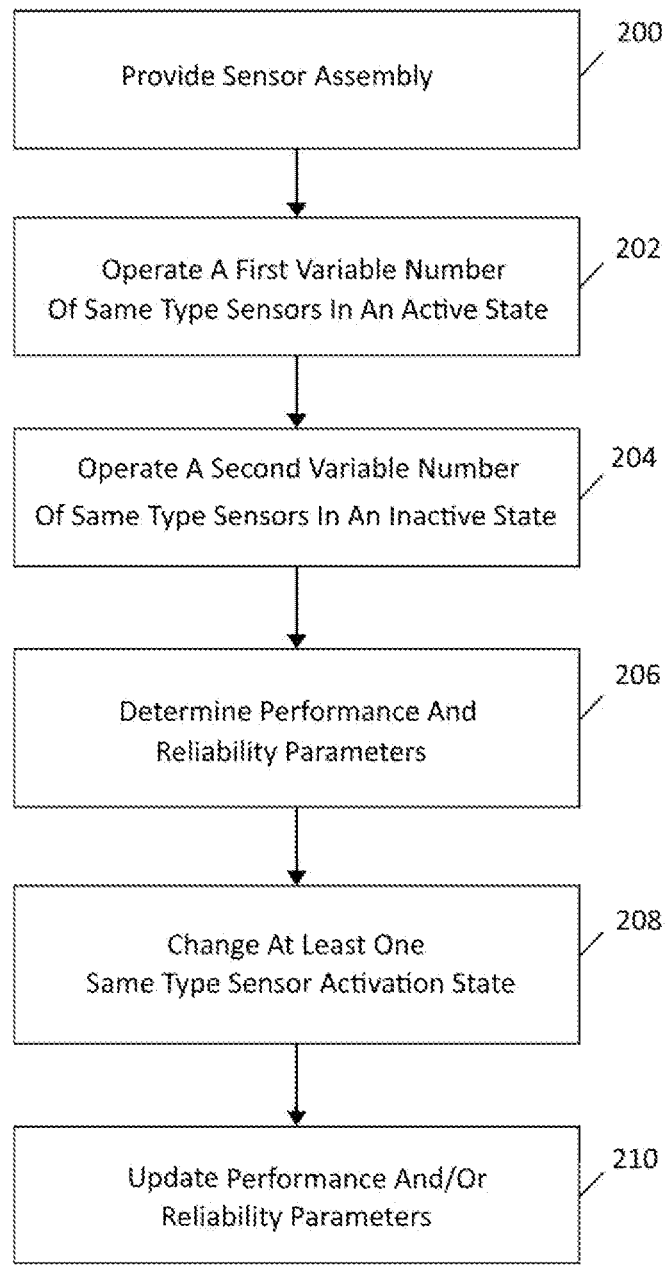
FIG. 2 is an exemplary routine for changing the activation state of the same type sensors according to an embodiment.

To help illustrate aspects of this disclosure, an exemplary routine is schematically depicted in FIG. 2. Beginning with 200, a sensor assembly is provided that has a plurality of same type sensors as noted above. In 202, a first variable number of the same type sensors are operated in an active state and in 204, a second variable number of the same type sensors are operated in an inactive state. Generally, the first variable number and the second variable number sums to the total number of same type sensors in the assembly. A performance parameter and/or a reliability parameter are determined in 206, based at least in part on the first and second variable numbers. As an illustration, the performance parameters and/or reliability parameter can be compared to an initial state or any other predefined or nominal state. These parameters may also reflect other characteristics as desired. For example, the performance parameter may also reflect a performance level if the sensor is capable of variable operational states, such as at different noise levels or sampling rates, its accuracy as compared to the output of other sensors, or any other suitable information. Similarly, the reliability parameter can include information such as when and how often anomalies have occurred, whether recovery has been attempted and whether it has been successful, an estimated time to failure, and other metrics as warranted. Next, in 208, the activation state of at least one of the same type sensors is changed based on an operational parameter. For example, the operational parameter may reflect a desired balance between performance and reliability and an inactive sensor can be transitioned to an active state or vice versa to maintain or achieve that ratio. Further, since "active" and "inactive" can encompass additional characteristics beyond being powered on or not, the change in activation state can also include any adaptation of how the sensor operates as may be indicated by the operational parameter. As a result of the change in activation state, at least one of the performance parameter and the parameter is updated in 210.

The operational parameter may also be used to accommodate environmental conditions that may affect each of the same type sensors differently. For example, MEMS sensors may exhibit small manufacturing variations that result in differential behavior even when exposed to the same conditions. In the context of powered devices that employ a motor, engine or any other system operating at one or more frequencies, one sensor may resonate at a given frequency while another may not. As will be appreciated, such resonance may result in anomalous behavior of the affected sensor. This phenomenon is common to any mechanical/electrical devices that experiences vibration and may benefit from conditional based monitoring (CbM) to improve performance and/or reliability by assessing the effects of the vibration. Consequently, the operational parameter may be used to indicate this condition for an active sensor so that it can be replaced with a previously inactive sensor that does not experience the same resonance perturbation. It should be appreciated that these techniques can be extended to cover other environmental conditions that may affect each same type sensors in a different manner.

Figure 3:
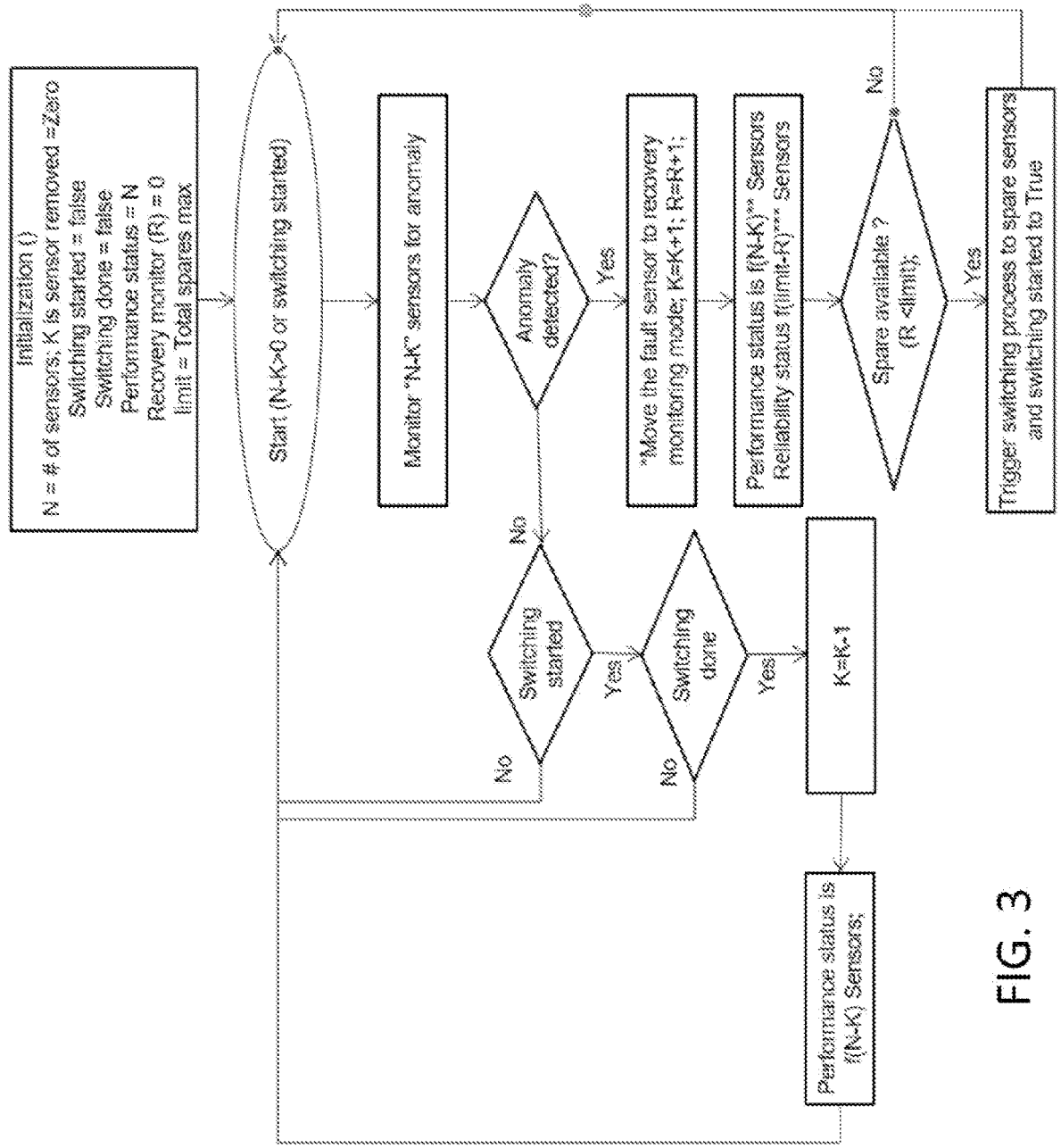
FIG. 3 is an exemplary routine for monitoring a plurality of same type sensors according to an embodiment.

From the above, it will be appreciated that embodiments of this disclosure facilitate maintaining a sensor assembly at a desired level of performance by replacing a temporarily or permanently faulty sensor by activating a reserve sensor of the same type. An exemplary routine for performing this switch, such as may be performed by control module 122, is schematically depicted in FIG. 3. As shown, an initialization step to establish the starting configuration of the sensor assembly begins the routine, based on how many same type sensors are active. As noted above, one criterion for this selection may be the desired performance level of the sensor assembly. By activating multiple same type sensors, their measurements can be combined or compared to improve accuracy. Alternatively, greater reliability can be achieved by reserving more same type sensors in an inactive state so that they can replace an active sensor that experiences an anomaly or fault, requiring it to be temporarily or permanently inactivated. In generally, performance and reliability may be balanced against each other by selecting the first variable number of active sensors and the second variable number of inactive sensors as discussed above. In this routine, N is set to the number of active same type sensors. In the initial state, no sensors have failed, so the number of removed sensors K (i.e., changed to an inactive state) is set to zero. Switching started and switching done flags are set to false. In one aspect, the performance parameter depends at least in part on the number of activated sensors, as indicated by setting the performance status to N. The number of same type sensors initially in inactive states to serve as spares establishes the limit value, the number of sensors that can be replaced. The variable R serves to monitor the recovery status of a removed sensor, an operation discussed in further detail below.

Following initialization, the routine begins as indicated when the number of active sensors, N, less the number of removed sensors, K, is greater than zero or when the switching started flag is true. Correspondingly, the N−K sensors are monitored for anomaly. For example, the output of one sensor can be compared to the others and if there is a deviation of more than a threshold, it may be determined the sensor is not operating correctly. When anomalous behavior is detected, the affected sensor is removed and considered to be in an inactive state so that its measurements are not used with the outputs from the remaining active sensors. As indicated, K and R are both incremented by one. Next, the performance parameter and the reliability parameter are updated, such as by evaluating the performance status as a function of N−K, the number of initially activated sensor minus the number of removed sensors, and by evaluating the reliability status as a function of the remaining reserve sensors, given by the limit minus R, the number of reserve sensors that have been activated to replace sensors experiencing anomalies.

The routine then branches depending on whether spare sensors of the same time are available, that is, when R is less than the limit. If no spares are available, the routine returns to the beginning and the remaining active sensors are monitored as discussed above. However, when reserves are available, the switching started flag is set to true and one of the spare sensors is transitioned from an inactive state to an active state. For example, samples can be given a lower weight or ignored while the switching started flag is true in case transient anomalies are associated with that time period. More generally, data obtained while the switching started flag is true can be identified and dealt with as warranted.

The above discussion follows the routine when one of the monitored N−K sensors is experiencing an anomaly. As indicated in FIG. 3, when an anomaly is not detected, a first check is performed to determine if the switching flag is set to true. If not, the route cycles to the beginning and if so, then checks to determine if the spare sensor has been successfully transitioned to being active. If not, again the routine cycles to the beginning. Upon completion of the switch, the switching done flag is set to true, so that check then proceeds to decrement K by one, since the removed sensor has been replaced. The performance parameter is again updated, such as by evaluating the performance status using the new value of N−K and the routine can again cycle to the beginning. From the above, it will be appreciated that the status of the sensor assembly can readily be determined based on the variables of the routine, including the whether any switching of sensors has been performed, whether the assembly is operating at its nominal performance level (i.e., when K is zero), how many reserve sensors remain (limit minus R), and other suitable characterizations.

Figure 4:
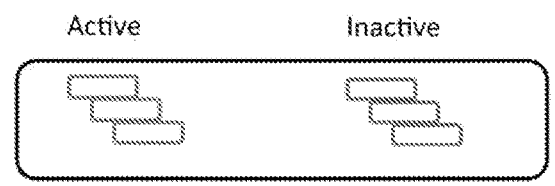
FIG. 4 is schematic diagram of a sensor assembly having a configuration of active and inactive sensors according to an embodiment.
Figure 5:
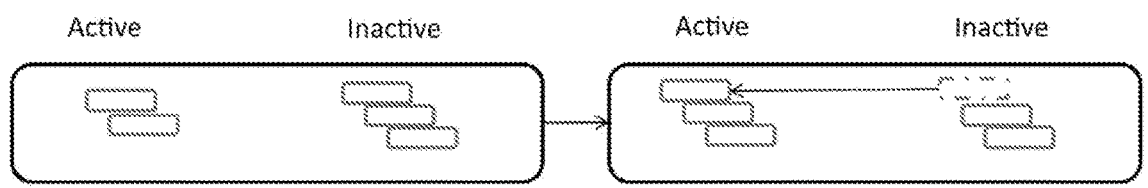
FIG. 5 is schematic diagram showing the transition of an inactive sensor to an active sensor according to an embodiment.
Figure 6:
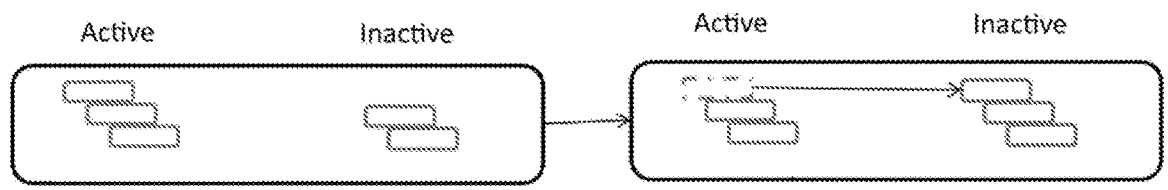
FIG. 6 is schematic diagram showing the transition of an active sensor to an inactive sensor according to an embodiment.

By following the above routine, reserve sensors of the same type can be activated to replace an initially active sensor that becomes defective. As discussed, this switch affects either or both the performance parameter and the reliability parameters. As one illustrative example, FIG. 4 schematically depicts the initial configuration of a sensor assembly having six of the same type sensors. There are three active sensors and three inactive spare sensors. For a system intended to combine the outputs of three same type sensors, this can be viewed as representing 100% performance since three sensors are active and 100% reliability as there is a backup for each of the three active sensors. Next, FIG. 5 schematically depicts the switching that is performed when an anomaly is detected in one of the active sensors. In the left configuration, before the transition, only two active sensors are available representing a relative 67% performance level given that one sensor was not performing correctly and was removed, but there are still three sensors in reserve, so there is still 100% reliability. After transition, as indicated by the right configuration, there are once more three active sensors yielding 100% performance, but the relative reliability has been reduced to 67% as there are now only two spares. Further, FIG. 6 schematically depicts a further adjustment that could be performed as desired. Specifically, the left configuration of FIG. 6 shows the result of the transition from FIG. 5, such that one of the active sensors could be returned to an inactive state to function as a spare to match the left configuration of FIG. 5, with the reduction to 67% performance but returning to 100% reliability. The indicated switch or reverse switch of FIGS. 4-6 can be performed automatically or as selected by a user. It will be appreciated that depending on how the sensor assembly is being employed, reliability or performance may take precedence. For example, during navigational applications, performance might be preferred, while other applications, such as platform stabilization or other safety-oriented operations, reliability might be preferred. The techniques of this disclosure allow either aspect to be optimized, including by setting the initial numbers of active and inactive sensors out of the total of same type sensors. Moreover, allocation can be dynamically changed as warranted by the current usage of the sensor assembly. The operational parameter used may be configured to reflect the desired balance between performance and reliability parameter, so that sensors are selectively activated and deactivated as warranted. As an illustration, under conditions when the sensor assembly is experiencing greater motion, some finer measurements may be overwhelmed by the larger forces, which can favor using an operational parameter that emphasizes reliability rather than performance. Corresponding adjustments to the operational parameter can be made based on current conditions and/or historical usage patterns, for example. Configuration of the sensor assembly may also be done based on the obtained sensor data, so as to automatically adjust to the context of usage. For example, sensor data often close to the full range of the sensor output may indicate an increased risk of sensor damage or malfunction, and therefore reliability may be preferred over performance. On the other hands, when sensor data is in a lower range, perhaps close to the noise level, performance may be preferred to increase the signal to noise ratio. As another example, if design performance exceeds that needed for a given purpose, reliability could be adjusted to be emphasized. To illustrate, performance can be compared to predefined specification or operational parameters, and if the performance is better than needed, the sensor operated is adapted to increase reliability while still maintaining the required performance (but without excess performance).

The routine discussed above involves monitoring the active sensors for anomalies. As noted, this can be done using the outputs of the other active sensors, but any suitable technique may be used as desired. For example, a reserve or otherwise inactive sensor can also be used to verify operation of the active sensors or information from other sensors can help identify anomalous behavior. Comparing data from different sets of sensors can be used to identify which sensor is not performing correctly. As desired, this monitoring can be performed as a self-test in real time. Further, the monitoring may also involve other signal analysis techniques, such as by assessing signal to noise ratio (SNR), variance in output, or any other suitable metric. These characteristics can also be compared to expected design values to help gauge sensor performance and/or reliability. Such monitoring may include identifying which sensors may be differentially affected by environmental conditions, such as when one sensor experiences resonance at an operating frequency of the device. It will also be appreciated that the anomalous behavior may be temporary. For example, a device having a motor (e.g., driving the rotors of an aerial drone) may cycle through a range of frequencies depending on the output of the motor. Different iterations of the same type sensors may experience resonance at different frequencies across that range and therefore be replaced temporarily as warranted. As noted, identification of anomalous behavior can be performed by comparing the outputs of the same type sensors. Further, to the extent the effect of the environmental condition is reproducible, that behavior can be learned so that the sensor can be proactively replaced when those conditions exist or are expected rather than waiting for an analysis of the sensor output to indicate anomalous behavior.

Moreover, the techniques of this disclosure also include reporting the current status of one or more of the sensors. The above example is given in the context of a binary determination of whether an anomaly exists, such that the sensor output is considered valid and used with the other active sensors or the sensor output is considered invalid and discarded. However, more detail can be provided to help refine the behavior of the system. For example, intermediate failure levels such as when known failures have occurred but the sensor performance appears unaffected, or when known failures have occurred and sensor performance has degraded but may still be useful depending on the situation. As will be appreciated, any or all of this information may be reflected in the performance parameter and/or reliability parameter. Reporting of sensor status can also include information specific to the type of sensor being used, such as a gyroscope or an accelerometer. Still further, the information reported can include a history of past status, including the number and timing of detected anomalies. Each sensor can report information regarding its status at desired intervals, such as every 1 or n samples, and/or in response to an external request. The reporting may include attaching the information to the data samples or may be delivered in a separate stream. Any suitable information reported by the sensors may be used to adjust the operational parameter and thereby control the change in activation state of the plurality of same type sensors.

As noted, the sensor assembly achieves improved performance by utilizing the outputs of more than one same type sensors. In general, accuracy is improved by combining the independent outputs of each active same type sensor. Although this combination can be a simple averaging operation, selectively weighting may be employed as desired. For example, the information reported by the sensors regarding their status includes performance and reliability characteristics, which may in turn be used when combining their outputs. As a relatively straightforward illustration, sensors known to have failures or other anomalies may receive relatively less weight than sensors that do not, but more sophisticated techniques can be applied as warranted.

The techniques of this disclosure also accommodate the possibility of failure recovery. Notably, depending on the type of anomaly, the failure of a sensor may be temporary rather than permanent. Accordingly, it may be desirable to continue to monitor a sensor that has been transitioned to an inactive state as a result of anomaly detection to determine if it is able to resume function. Such monitoring may include checking the output of the sensor that experienced the anomaly against the remaining active sensors and determining its status based on the comparison. For example, the moveable sensitive elements of a sensor may become stuck, a condition typically referred to as stiction in accelerometers and stall in gyroscopes. When in this condition, a thermal or physical shock may be sufficient to allow the stuck element to resume normal operation. The thermal or physical shock may be result from environmental conditions or it may be actively induced using an actuator associated with the sensor assembly, such as actuator 124 noted above. If several recovery strategies are enabled, the selected recovery method may depend on the anomaly characterization or analysis. If recovery is not successful, the recovery may be attempted at a later stage. The success of sensor recovery may then be assessed, such as by using similar techniques to those described above for anomaly detection. Further, it may also be desirable to perform a calibration operation on the recovered sensor. Again, the presence of multiple same type sensors facilitates calibration since the function of the recovered sensor can be directly compared to the output of the other active (or inactive) sensors without the need to wait for or impart specific motion conditions that would be needed to calibrate a single sensor.

Figure 7:
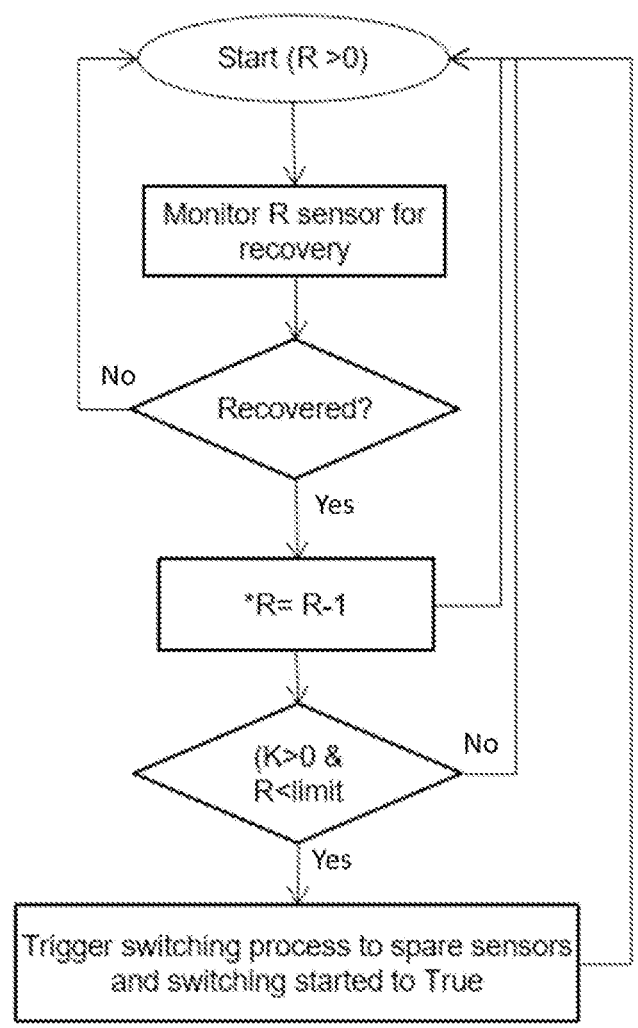
FIG. 7 is an exemplary routine for monitoring recovery of a sensor according to an embodiment.

To help illustrate suitable techniques for sensor recovery, FIG. 7 schematically depicts an exemplary routine. Although described as being performed in conjunction with the routine of FIG. 3, it may be adapted to any other suitable routine. Notably, it may be desirable to defer the recovery to a more opportune time, such as when the motion conditions are favorable. As discussed above, detecting an anomaly results in incrementing the recovery monitor variable R. Correspondingly, this routine may begin when R is greater than zero. The affected sensor is then monitored for recovery, such as being assessed in comparison to other active sensors as described. If recovery has not been achieved, the routine cycles to the beginning so that monitoring of the sensor can continue. If the sensor has recovered, R decrements by one to indicate that the failed sensor has recovered and can operate in active state again. A check is performed to confirm that a sensor's output has been removed from the assembly output as indicated by K being greater than zero and that spare sensors are available as indicated by R being less than the limit. If either condition is not met, the routine cycles to the beginning. Otherwise, the switching process to re-activate the monitored sensor is triggered and the switching started flag is set to true. In some situations, it may be desirable to revert to the recovered sensor, such as if the primary active sensors offer relatively improved performance as compared to the inactive sensors held in reserve.

Accordingly, there may be some degradation in performance when using the reserve sensor which can be regained by reverting to the original sensor if it is successfully recovered.

To facilitate the proper characterization of a sensor that may be experiencing anomalous behavior, it can be desirable to distinguish between conditions that reflect a mechanical problem occurring in the sensor operation, such as a stuck element in the case of stiction or stall, from conditions that exceed the capabilities of the sensor, such as when it becomes saturated and is unable to detect further changes in the phenomena being measured. Examples of suitable techniques include checking for deviation against other active or inactive sensors and detecting an anomaly if the deviation is larger than a threshold over a period of time. Further, the noise density of the sensors can be compared to each other, with an appropriate update to the performance parameter and/or reliability parameter depending on whether the comparison indicates failure or performance degradation. Stiction or stall can be identified when the output is at the same value for a period of time if that value does not correspond to the full-scale range (FSR) of the particular sensor. Similar, if the value being output is at the sensor's design limit, it is possibly in a saturated condition and has not otherwise failed, but it could also be stuck at that limit. Correspondingly, an additional check may be performed, such as by comparing the outputs of the other same type sensors. If the monitored sensor does not deviate by more than a threshold from the others, it may be considered to be saturated but if there is significant deviation, it may be stuck. Alternatively or in addition, outputs from other types of sensors can help distinguish between these conditions. For example, gyroscope data showing no motion can help determine that an accelerometer is stuck at its limit. Similarly, accelerometer data within a threshold from the expected force of gravity can also indicate that a gyroscope outputting values at its FSR is stalled rather than saturated. As with the other information reported by the sensors, the characterization of sensor anomaly may also be used when setting the operational parameter.

The above material discusses the operational parameter in the context of achieving desired performance and/or reliability for the sensor assembly. In addition, the operational parameter may reflect other aspects of the sensor assembly function. For example, the Mean Time To Failure (MTTF) of the entire sensor assembly may be assessed. This value is increased when only some sensors are active, while the others are inactive. As such, the operational parameter may be used to tailor the expected lifespan of the sensor assembly to the specific application for which it is used. MTTF can also be assessed for individual sensors of the assembly as desired. More generally, any aspect of performance and reliability change over time may be predicted, such as by extrapolating any suitable threshold chosen to define as failure. Further, information reported about the sensor status, including its performance in comparison to other same type sensors and/or other characteristics may be used to estimate time to failure for individual sensors as well as the sensor assembly as a whole. As another example, regulations might impose required limits on sensor performance, and the operational parameter can be configured to keep operation within those limits. As yet another example, the operational parameter can reflect a desired level of power consumption, such that the activation states of the plurality of same type sensors may be set accordingly. The operational parameter may also be used to mitigate interference between sensors. For example, if activating a particular configuration of the same type sensors (e.g., all of them), the operational parameter may be established to activate subsets that do not create interference.

The techniques of this disclosure also include provisions for reducing disruptions caused when switching out an active sensor with an inactive sensor that has been held in reserve. In particular, the sensor outputs may be subject to various kinds of preprocessing before use, including corrections based on calibration such as bias and sensitivity. As one illustration, changing from one sensor to another sensor of the same type has the potential to create a discontinuity in the output due to the different biases of the sensor. This can be mitigated by determining whether the sensor assembly is experiencing motion during the switch. If so, a bias shift adjustment is not required. If not, however, and adjustment for the bias shift is then applied. Notably, the difference of bias between the prior and current sensor can be added as an adjustment to the output until the sensor assembly resumes motion. Similar techniques may be employed for any preprocessing of sensor information that is specific to the particular sensors involved.

From the above, it will be appreciated that the techniques of this disclosure include a method for controlling a sensor assembly that involves providing a sensor assembly having a plurality of same type sensors, operating a first variable number of same type sensors in an active state, operating a second variable number of same type sensors in an inactive state, and an activation state of at least one of the plurality of sensors may be changed based at least in part on an operational parameter, wherein the operational parameter relates to an environmental condition differentially affecting the plurality of same type sensors.

In one aspect, the operational parameter relates to an operating frequency of a device incorporating the sensor assembly.

In one aspect, performance may be increased by activating at least one sensor.

In one aspect, reliability may be increased by deactivating at least one sensor.

In one aspect, the operational parameter is determined based on output of the sensor assembly.

In one aspect, the operational parameter may be an anomaly status for at least one of the plurality of sensors. The anomaly status may be characterized. The anomaly status may be correlated to the environmental condition.

From the above, this disclosure is also directed to a sensor system comprising a plurality of same type sensors and at least one processor. The at least one processor may be configured to operate a first variable number of sensors in an active state, operate a second variable number of sensors in an inactive state and change an activation state of at least one of the plurality of sensors based at least in part on an operational parameter, wherein the operational parameter relates to an environmental condition differentially affecting the plurality of same type sensors.

Still further, this disclosure may involve a device with a sensor assembly comprising a plurality of same type sensors and at least one processor. The at least one processor may be configured to operate a first variable number of sensors in an active state, operate a second variable number of sensors in an inactive state and change an activation state of at least one of the plurality of sensors based at least in part on an operational parameter, wherein the operational parameter relates to an environmental condition differentially affecting the plurality of same type sensors.

In one aspect, the device has a system having at least one operating frequency. For example, the system may have a motor or engine. The operational parameter may relate to the operating frequency.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the present invention.

What is claimed is:

1. A method for controlling a sensor assembly comprising:
    a) providing a sensor assembly having a plurality of same type sensors;
    b) operating a first variable number of same type sensors in an active state, wherein the first variable number of same type sensors are not experiencing anomalies or faults and are greater than one such that output from a plurality of active sensors is combined;
    c) operating a second variable number of same type sensors in an inactive state; and
    d) changing an activation state of at least one of the plurality of sensors based at least in part on an operational parameter, wherein the operational parameter relates to an environmental condition differentially affecting the plurality of same type sensors.

2. The method of claim 1, wherein the operational parameter relates to an operating frequency of a device incorporating the sensor assembly.

3. The method of claim 2, wherein the operational parameter is determined
    based on output of the sensor assembly.

4. The method of claim 1, further comprising increasing performance by activating at least one sensor.

5. The method of claim 1, further comprising increasing reliability by deactivating at least one sensor.

6. The method of claim 1, wherein the operational parameter comprises an anomaly status for at least one of the plurality of sensors.

7. The method of claim 6, further comprising characterizing the anomaly status.

8. The method of claim 7, further comprising correlating the anomaly status to the environmental condition.

9. A sensor system comprising a plurality of same type sensors and at least one processor configured to:
    a) operate a first variable number of sensors in an active state, wherein the first variable number of same type sensors are not experiencing anomalies or faults and are greater than one such that output from a plurality of active sensors is combined;
    b) operate a second variable number of sensors in an inactive state; and
    c) change an activation state of at least one of the plurality of sensors based at least in part on an operational parameter, wherein the operational parameter relates to an environmental condition differentially affecting the plurality of same type sensors.

10. A device comprising:
    a) a sensor assembly comprising a plurality of same type sensors; and at least one processor configured to:
    a) operate a first variable number of sensors in an active state, wherein the first variable number of same type sensors are not experiencing anomalies or faults and are greater than one such that output from a plurality of active sensors is combined;
    b) operate a second variable number of sensors in an inactive state; and
    c) change an activation state of at least one of the plurality of sensors based at least in part on an operational parameter, wherein the operational parameter relates to an environmental condition differentially affecting the plurality of same type sensors.

11. The device of claim 10, further comprising a system having at least one operating frequency.

12. The device of claim 11, wherein the system comprises a motor.

13. The device of claim 11, wherein the operational parameter relates to the operating frequency.

* * * * *